(12) United States Patent
Chien et al.

(10) Patent No.: US 11,266,984 B2
(45) Date of Patent: Mar. 8, 2022

(54) MASSIVE MICROFLUIDICS FOR MULTIPLEXED COUNTING

(71) Applicant: The Board of Trustees of the Leland Stanford Junior University, Stanford, CA (US)

(72) Inventors: Jun-Chau Chien, Stanford, CA (US); Mohammad Amin Arbabian, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 653 days.

(21) Appl. No.: 16/053,696

(22) Filed: Aug. 2, 2018

(65) Prior Publication Data

US 2019/0039060 A1 Feb. 7, 2019

Related U.S. Application Data

(60) Provisional application No. 62/540,988, filed on Aug. 3, 2017.

(51) Int. Cl.
*G01N 33/49* (2006.01)
*G01N 15/00* (2006.01)
*B01L 3/00* (2006.01)

(52) U.S. Cl.
CPC .......... *B01L 3/5027* (2013.01); *B01L 3/50273* (2013.01); *B01L 3/502715* (2013.01); *B01L 3/54* (2013.01); *G01N 33/49* (2013.01); *B01L 3/502761* (2013.01); *B01L 2200/027* (2013.01); *B01L 2300/021* (2013.01); *B01L 2300/0636* (2013.01); *B01L 2300/0645* (2013.01); *B01L 2300/0864* (2013.01); *B01L 2300/0867* (2013.01); *B01L 2400/0409* (2013.01); *B01L 2400/0424* (2013.01)

(58) Field of Classification Search
CPC ........... B01L 3/5027; B01L 2300/0864; B01L 3/502715; G01N 33/49; G01N 15/00
See application file for complete search history.

(56) References Cited

U.S. PATENT DOCUMENTS

2019/0011349 A1* 1/2019 Bashir ................ G01N 15/1031

* cited by examiner

*Primary Examiner* — Brian J. Sines
(74) *Attorney, Agent, or Firm* — Foley & Lardner LLP

(57) ABSTRACT

A microfluidics device includes an inlet, a plurality of parallelized microfluidic channels, a splitter and a plurality of detection electrodes. The inlet receives a fluidic sample including biological particles. The parallelized microfluidic channels include interaction zones for analysis of the biological particles. The splitter transmits the fluidic sample into the parallelized microfluidic channels. Detection electrodes can conduct the analysis. Each detection electrode is shared among the parallelized microfluidic channels. The detection electrodes are spatially encoded electrodes arranged on locations of each of the parallelized microfluidic channels.

10 Claims, 18 Drawing Sheets

MASSIVE MICROFLUIDICS FOR MULTIPLEXED COUNTING

CROSS-REFERENCE TO RELATED APPLICATIONS

This application claims the benefit of and priority to U.S. Provisional Patent Application 62/540,988, filed Aug. 3, 2017, which is incorporated herein by reference in its entirety.

TECHNICAL FIELD

The present disclosure relates to devices and methods for analysis of biological particles, and more particularly to devices and methods using microfluidics for multiplexed analysis of biological particles.

BACKGROUND

Microfluidic devices based on micro-electromechanical technology are used in applications related to biology and medicine. A microfluidic device is an instrument that controls the behavior of small amounts of fluid through channels with small dimensions, e.g., the sub-millimeter range. Microfluidic devices can be designed to obtain analytical measurements such as molecular diffusion values, chemical binding coefficients, pH values, fluid viscosity, molecular reaction kinetics, etc. Microfluidic devices can be built on microchips (referred to as Lab-on-Chip) to detect, separate and analyze biological samples. For example, a microfluidic device may use body fluids or solutions containing cells or cell parts to diagnose diseases. Inside microfluidic channels, biological particles (e.g., including cells, beads, and macro-molecules) can be analyzed based on their optical, electrical, acoustic, and magnetic responses.

One type of biological particles are cancer cells that are found in circulation and are believed to disseminate from tumors and form secondary sites. These malignant cells, termed circulating tumor cells (CTCs), may provide a vital parameter for cancer detection, staging, and developing treatment for tumor metastasis. However, these cells occur within the body at low frequencies (1-10 CTCs/mL blood), are heterogeneous, and exist among billions of other blood cells (e.g., red blood cells (RBCs), and white blood cells (WBCs)). It is a challenge to perform liquid biopsy for CTCs (which are rare and heterogeneous) counts.

BRIEF DESCRIPTION OF THE DRAWINGS

Aspects of the present disclosure are best understood from the following detailed description when read with the accompanying drawings. It is noted that various features may not be drawn to scale, and the dimensions of the various features may be arbitrarily increased or reduced for clarity of discussion.

DETAILED DESCRIPTION

Figure 1:
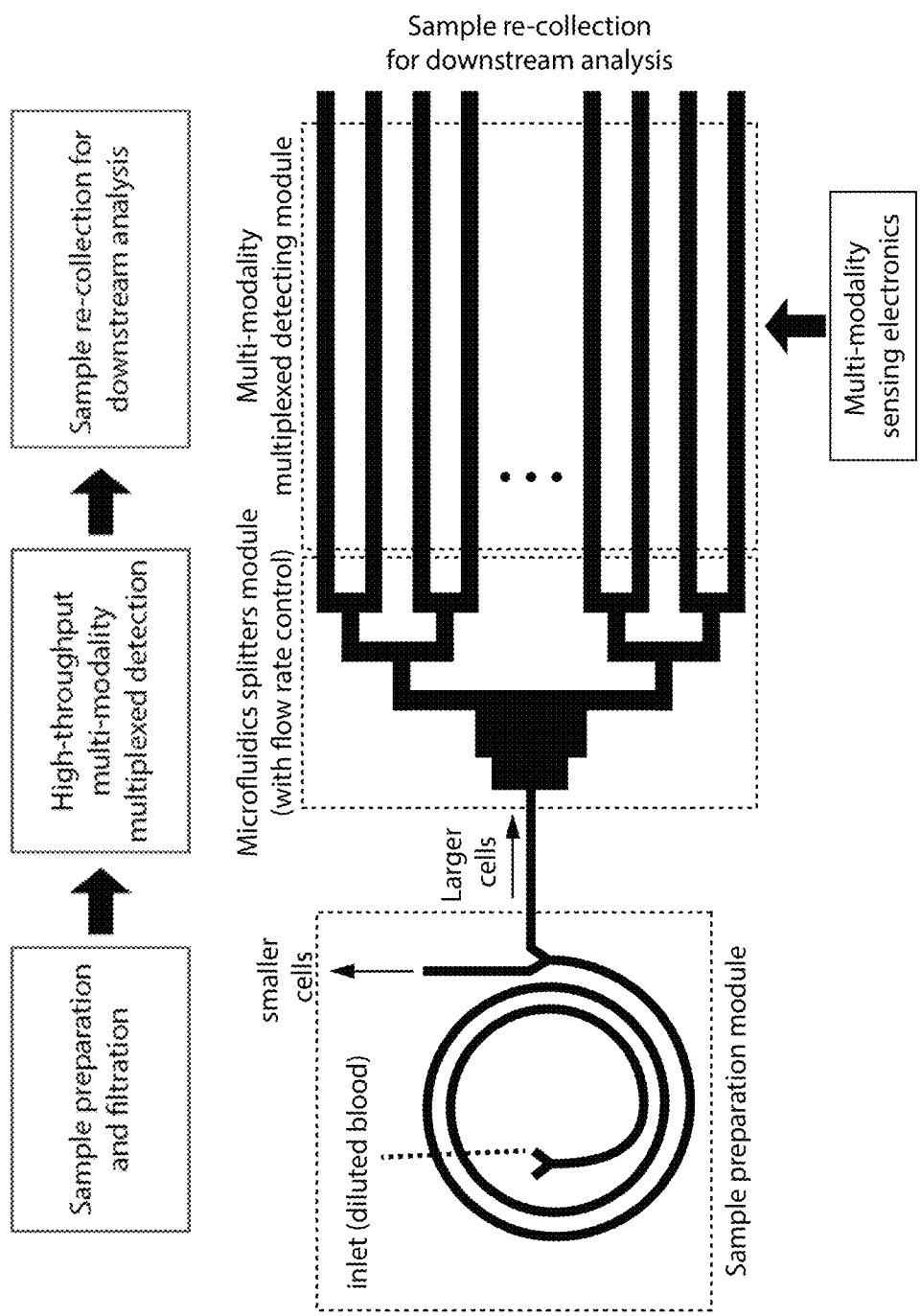
FIG. 1 illustrates a block diagram for a biological particle analysis device with multiplexing for high throughput.

Common reference numerals are used throughout the drawings and the detailed description to indicate the same or similar components. Embodiments of the present disclosure will be readily understood from the following detailed description taken in conjunction with the accompanying drawings.

Various embodiments of the present disclosure are discussed in detail below. It should be appreciated, however, that the embodiments set forth many applicable concepts that can be embodied in a wide variety of specific contexts. It is to be understood that the following disclosure provides many different embodiments or examples of implementing different features of various embodiments. Specific examples of components and arrangements are described below for purposes of discussion. These are, of course, merely examples and are not intended to be limiting.

Embodiments, or examples, illustrated in the drawings are disclosed below using specific language. It will nevertheless be understood that the embodiments and examples are not intended to be limiting. Any alterations and modifications of the disclosed embodiments, and any further applications of the principles disclosed in this document, as would normally occur to one of ordinary skill in the pertinent art, fall within the scope of this disclosure.

In addition, the present disclosure may repeat reference numerals and/or letters in the various examples. This repetition is for the purpose of simplicity and clarity and does not in itself dictate a relationship between the various embodiments and/or configurations discussed.

Liquid biopsy has drawn great attention as an alternative to comparative tumor biopsy due to its minimally invasiveness. One of the bottlenecks for its widespread use in clinics is the assay time and cost due to labeling reagents. In particular, circulating tumor cells (CTCs) are rare. Typically, there are only 1-5 CTCs presented in about 1 mL of whole blood. Therefore, the standard whole blood volume for CTCs counting is about 7.5 mL. Comparative CTCs counting specifies the enrichment of the targeted cells followed by detection and counting. Such a scheme has a low assay throughput and lacks multiplexed surface marker detection capability. CTCs detection raises additional challenges. A rapid analysis is specified for detecting CTCs. Otherwise target CTCs may become inviable and lose their phenotypes. The captured CTCs are to be viable for downstream molecular profiling.

For efficiently applying microfluidic technology to liquid biopsy, e.g. CTCs counting, it is desired to provide a system having a high assay throughput. The assay throughput is defined as the number of cells that can be measured for a given amount of time. Though the number of microfluidic channels can be scaled to large number through microfabrication, the inclusion of a large number of corresponding electronics for detection is not feasible due to size mismatch. The disclosed technology solves the problem by incorporating improved signal processing and hardware design to measure cells in large number of microfluidic channels using a significantly reduced number of electronic channels.

According to at least some embodiments of the present disclosure, a massive microfluidic technique is described to dramatically reduce the assay time without incurring excessive demands on the detection hardware. The system achieves a label-free multiplexed surface marker detection using transit-time analysis based on massive microfluidics for ultra-high-throughput flow cytometry. By coupling with label-free multiplexed surface marker detection based on cellular transit-time analysis, the detection specificity during the counting and sorting of circulating tumor cells (CTCs) in liquid biopsy is maintained.

According to at least some embodiments of the present disclosure, the massive microfluidic technique is applicable for droplets counting and analysis in droplet microfluidics.

In some embodiments, the system can be implemented in, e.g., a low-cost microfluidic Lab-on-Chip (LOC) for point-of-care. The system can be used for, e.g., liquid biopsy for cancer monitoring, whole blood cell counting, and cell searching from urine samples for infection and inflammation detection. The system can simultaneously achieve performance metrics including, e.g., high sensitivity, high specificity, multiplexed surface marker detection, low cost and small form factor, and reduced assay time.

In some embodiments, the system can achieve a performance metric, which is defined as a number of microfluidic channel multiplied by a number of surface markers that can be detected in a multiplex manner, normalized to a number of electronic channels of the detectors: $FoM = N_{fluidic} * N_{biomarker} / N_{detectors}$. A larger value of the FoM performance metric indicates that the system achieves a more efficient design. For example, for a system including one fluidic channel, one impedance measurement unit, and one surface mater, the FoM performance metric is 1. For a system including 1024 fluidic channels, 24 impedance measurement units, and 5 surface markers, the FoM performance metric is 213.

According to at least some embodiments of the present disclosure, an electronic-microfluidic integration technique allows an implementation of an ultra-high throughput flow cytometry having massively parallelized microfluidic channels (e.g., more than 100 channels). Comparative parallelized microfluidic channels are applicable to passive cell sorting using inertia microfluidics, in which active detectors are not included. However, such a scheme can sort cells based on size difference, lacking measurement specificity and accuracy. For example, the comparative techniques may not differentiate CTCs from WBCs, which have similar sizes. Therefore, it is desired to incorporate active sensors (such as photodetectors and electrical impedance sensors) in flow cytometry for multi-parametric measurements.

However, the integration of the active sensors within highly dense microfluidic channels raises the issue of the size mismatch between the fluidic channels and the electronic detectors. Specifically, the size of each electronic detector is comparable to the lateral dimension (or width) of the microfluidic channel in comparative devices. In addition, the routing of the input/output (I/O) wires from each detector is challenging, as hundreds or even thousands of wires are distributed across the entire chip, causing crosstalk among different electronic channels.

Another bottleneck of passive cell sorting technique is the low detection specificity. For example, there is no significant size difference between leukocytes and circulating tumor cells, which can lead to high false positive or false negative depending on the detection threshold. Comparative approach for high specificity measurement is to label the target cells based on cellular surface biochemistry. The fluorophores or magnetic particles are conjugated with specific antibodies that show high affinity to the target surface biomarker (antigen). The sample is incubated followed by measurements of the labels using fluorescence or magnetic detection. Such a sample preparation step can be time consuming and can be the rate-limiting step in comparative fluorescent active cell sorting (FACS) or magnetic-activated cell sorting (MACS). In addition, FACS and MACS involve RBC lysis, which is not desirable and may alter CTCs.

According to at least some embodiments of the present disclosure, the sample preparation step can be eliminated by measuring the transient interaction between the targeted surface markers and the corresponding antibodies coated along the walls of the microfluidic channels, referred to as the interaction zones. When the target surface marker is presented on a cell, the interaction incurs a drag force that reduces its flowing velocity. This reduction in velocity, which is an indirect indication of the existence of the targeted surface biomarker, can then be detected through the transit-time analysis. For example, one example of the transit-time measurement is to record the time difference between a cell entering and leaving an interaction zone. In this context, two detectors can be sufficient. Multiple interaction zones with different antibodies can be introduced within a single microfluidic channel. This allows multiplexed surface markers detection at single cell level.

According to at least some embodiments of the present disclosure, the multiplexed techniques is applicable for nanofluidics applications for molecular analysis including DNA sequencing and molecular sensing. Coding can be embedded directly in the nucleotides using synthesis approach by randomly or specifically designed the sequence that composed of adenine (A), thymine (T), guanine (G), and cytosine (C). The detection of sequence, and thus the codes, can be performed using nanopore technologies.

FIG. 1 illustrates a functional block diagram for a biological particle analysis device with multiplexed identification and detection for ultra-high throughput. The device can include three major functionalities: filtration, multiplexed detection, and downstream analysis. During the detection, samples are split into multiple channels for throughput enhancement. However, integrating dedicated detection sensor such as image sensors and impedance analyzers in each microfluidic channel is neither inefficient nor possible due to densely packed microfluidic channels. Therefore, multiplexing techniques are introduced to enable more efficient implementation of the electronics.

Figure 2:
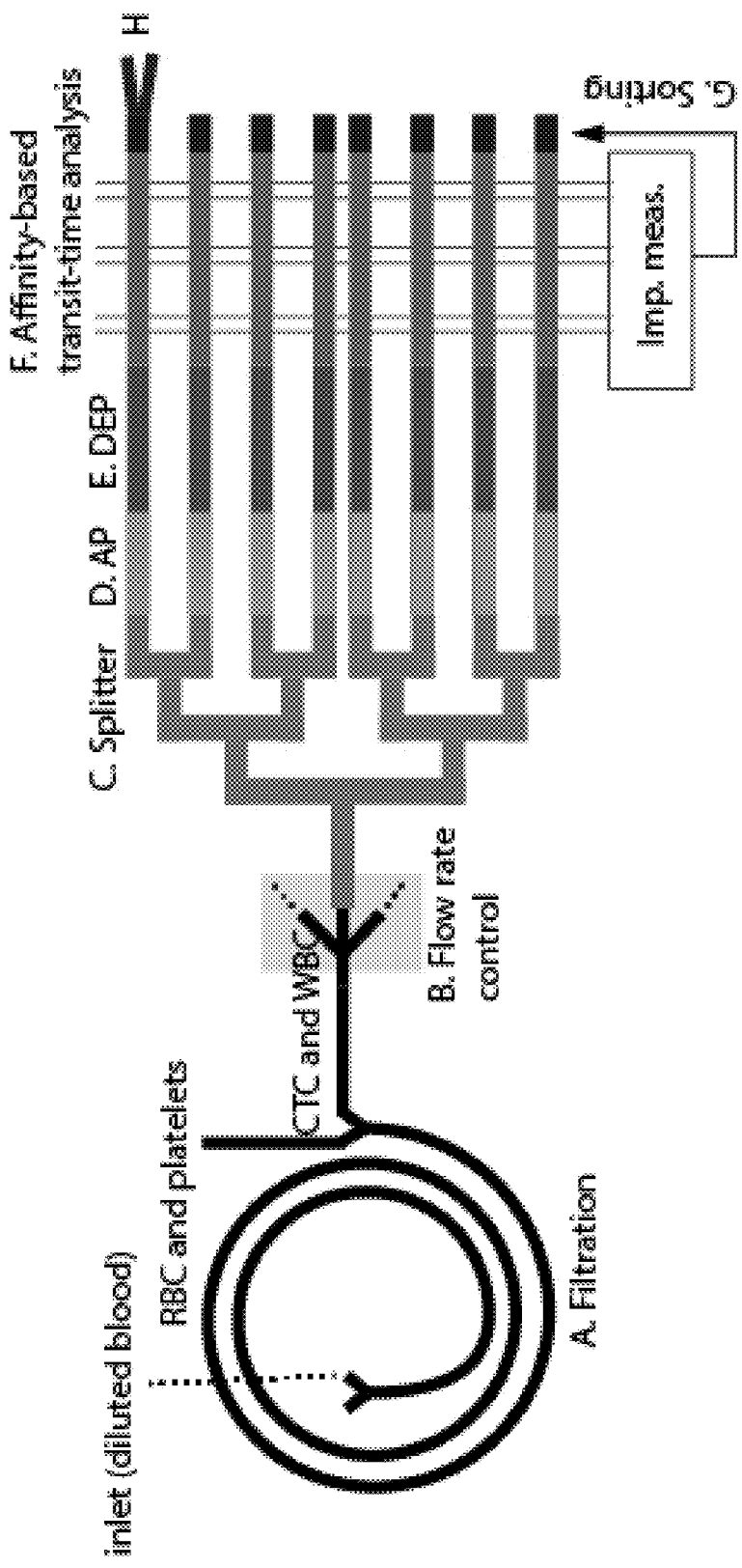
FIG. 2 illustrates an example of a biological particle analysis device.

FIG. 2 illustrates an example of a biological particle analysis device. The device includes multiple parts. Part A performs filtration using inertia flow fractionation at high-throughput (e.g., cellular velocity>200 mm/sec, flow rate>1 mL/min). Part B performs flow rate control, for slowing down the cell velocity. Part C is a splitter for parallelism to multiple channels (e.g., 128, 256, or 1024 channels). The cellular velocity in the channels may be, e.g., about 1 mm/sec. Part D performs acoustophoresis, for focusing the cell to the center of the channel. Part E performs nDEP (negative dielectrophoresis) actuation, actively focusing the cells toward the floor of the fluidic channel. Part F performs affinity-based transit-time analysis using impedance analyzer, which may include multi-frequency spectroscopy for, e.g., 8 frequencies spanning about 0.1 MHz to about 1 GHz. Part G may perform sorting of the biological particles. Part H may perform further downstream analysis, such as FACS, or DNA sequencing. The disclosed system may include or may not include part H.

The biological particle analysis device can achieve a massive microfluidic implementation by introducing multiple degrees of freedom in the design. For example, inertia microfluidic or hydrodynamic focusing, performed by, e.g., the flow rate control, can focus the particles (e.g., cells) into a single stream. When the single stream is split into multiple streams and enters multiple fluidic channels, a delay can be introduced between each particles. The delay can be registered by the first detection electrode in each channel. In other words, the delay of each individual particle entering the fluidic channel can be predetermined and can be a degree of freedom adjusted by the system. In some embodiments, other degrees of freedom may include spatial coding of electrode sequence, cell-specific coding, and interleaving block codes, which are discussed in subsequent passages.

In some embodiments, the disclosed system may utilize a transient cell-molecular interaction as the sensing mechanism. A dynamic interaction of surface marker with the antibodies (or aptamer) coated surface leads to a change of flow speed. A change of flow speed is detected by measuring the transit time between cells entering and existing the interaction zone. Different antibodies may be coated at several zones for biomarker multiplexing. In addition to antibodies, other types of molecular recognition molecules such as aptamers can be used in a similar way. Cells may be specified to flow at a low speed (e.g., about 1 mm/sec). If the flowing speed is too fast, the interacting effect may not be pronounced. If the flowing speed is too slow, cells may be captured and immobilized by the coated surface.

Figure 3:
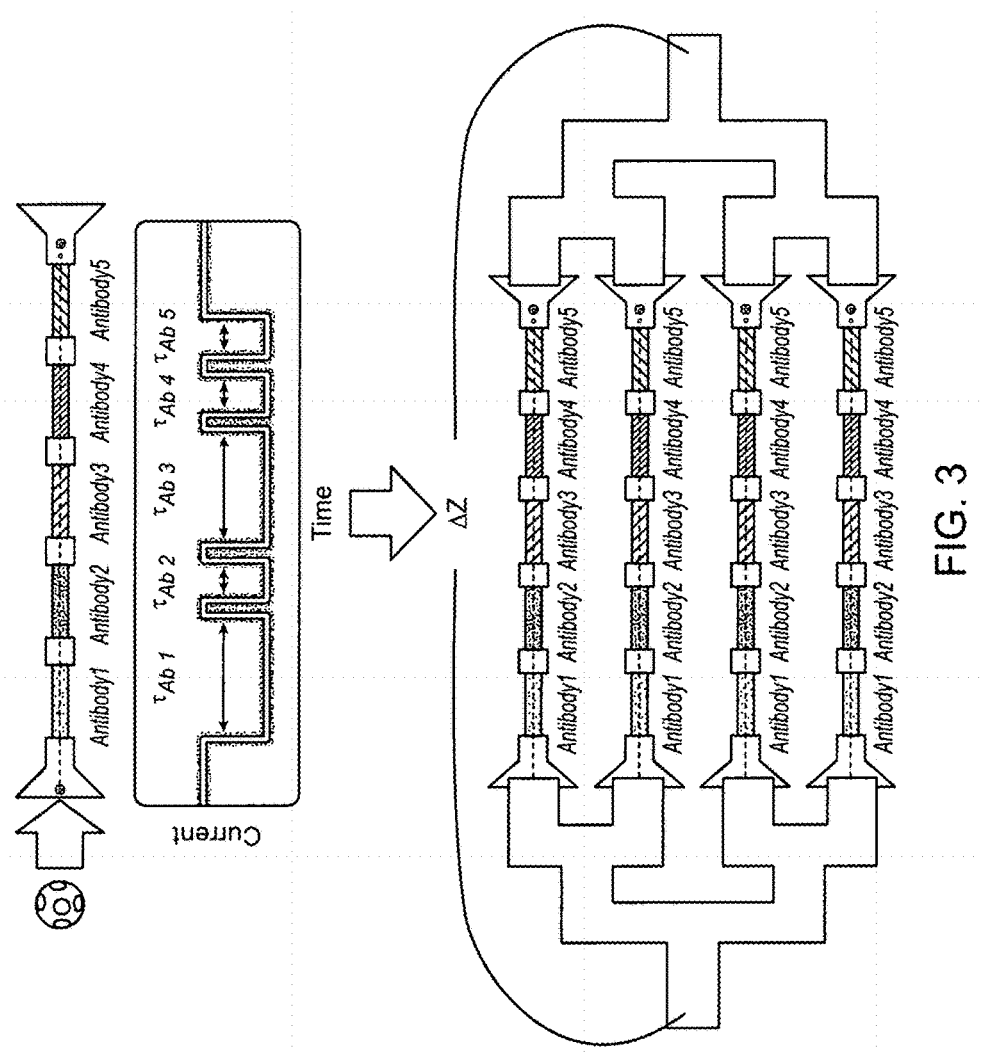
FIG. 3 illustrates parallelized multiple channels in node-pore microfluidics.

If the process is performed by a single channel, the throughput may be as low as, e.g., 10 cells/sec, which corresponds to 277 hours for processing 1e7 cells (from about 1 mL of whole blood). FIG. 3 illustrates parallelized multiple channels. However, the parallelism may not be applicable since cells in different channels are not differentiable from the measured pulsed signals due to inter-channel interference.

Figure 4:
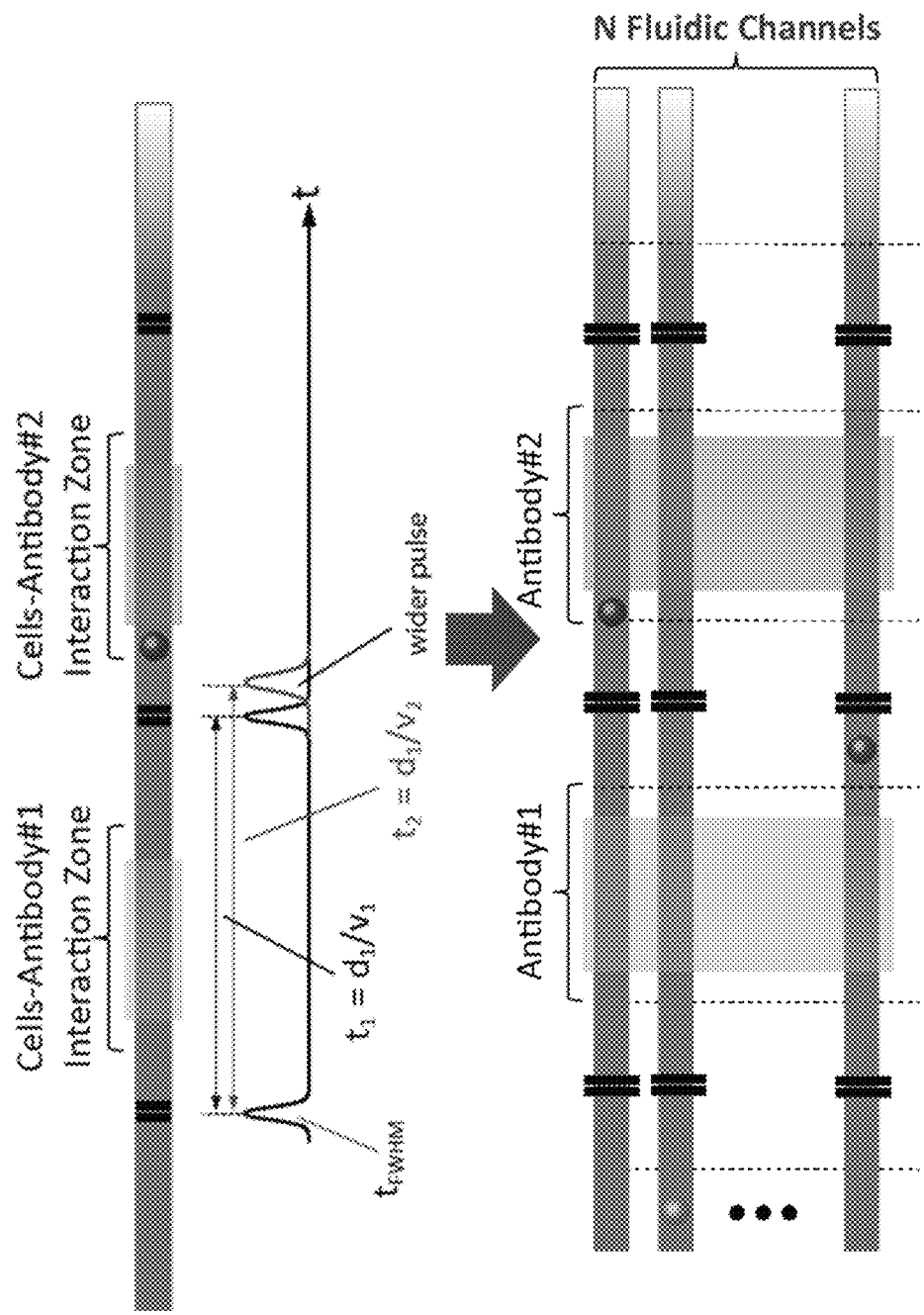
FIG. 4 illustrates parallelized multiple channels with a multi-electrode configuration for cellular transit-time analysis.

In some embodiments, the system can utilize a parallelism in a multi-electrode mechanism. FIG. 4 illustrates parallelized multiple channels with a multi-electrode mechanism. Multi-coplanar electrodes are distributed along the microfluidic channel, segmenting different cells-antibody interaction zones. As shown in FIG. 4, instead of having one detector per fluidic channel, a pair of coplanar electrodes is extended across all the microfluidic channels. Impedance measurement is performed on the electrodes, which generates Gaussian-like pulses as cells flow through. However, scaling the number of detection electronics corresponding to the number of microfluidic channels is not hardware-efficient and is challenging. For example, 1000 channels with 5 antibody interaction zones can lead to 6000 electronics. It is also infeasible to integrate each electronics within the fluidic channel due to size constraint. Note that cellular biomarker detection can be promoted not only with antibodies but also with aptamers.

In some embodiments, as shown in the top part of FIG. 4, due to a random variation in particle flowing velocities, a wider pulse may be observed at the end of interaction zone. The wider pulse may introduce uncertainty in the subsequent transit-time analysis. To eliminate or minimize the uncertainty, the system may normalize the transit time for the detection of targeted particles (e.g., cells). For example, the transit time $t_2$ as shown in FIG. 4 can be normalized by: $t_2/t_{FWHM}$. This is because the pitch between a pair of co-planar electrodes and the distance between pairs of electrodes may be determined by design and served as geometrical reference. Alternatively, the $t_{FWHM}$ measured from a single Gaussian pulse using a pair of co-planar electrodes can be replaced with, e.g., three-coplanar-electrode configuration, in which the reference transit time is extracted from the time difference between the peaks of the measured bipolar pulses. Thus, the configuration of bipolar pulsing introduces one extra degree of freedom by encoding the measured pulse with, e.g., either positive or negative sign.

Figure 5:
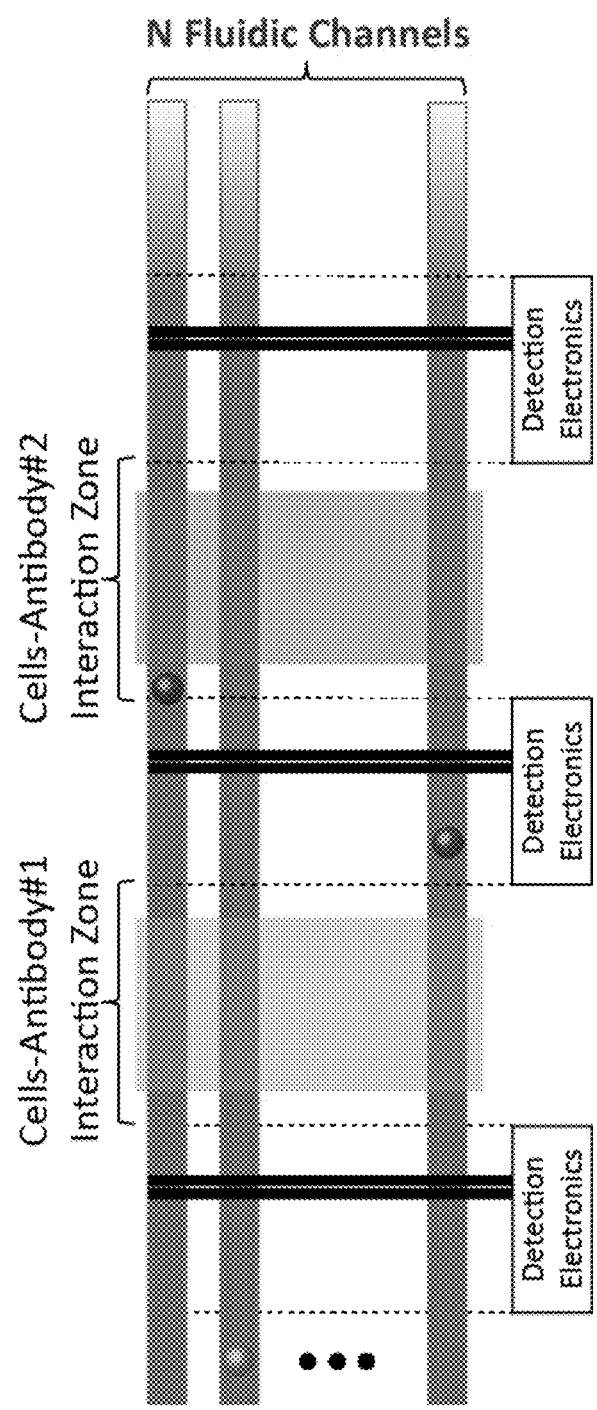
FIG. 5 illustrates parallelized multiple channels with a multi-electrode configuration for transit-time analysis with shared detection electronics.

In some embodiments, the channels of the system may share the detection electronics. FIG. 5 illustrates parallelized multiple channels sharing detection electronics. However, this leads to the inter-channel interference issue as shown in FIG. 3. Cells or other particles in different microfluidic channels are not differentiable from the measured electronic pulses.

Figure 6:
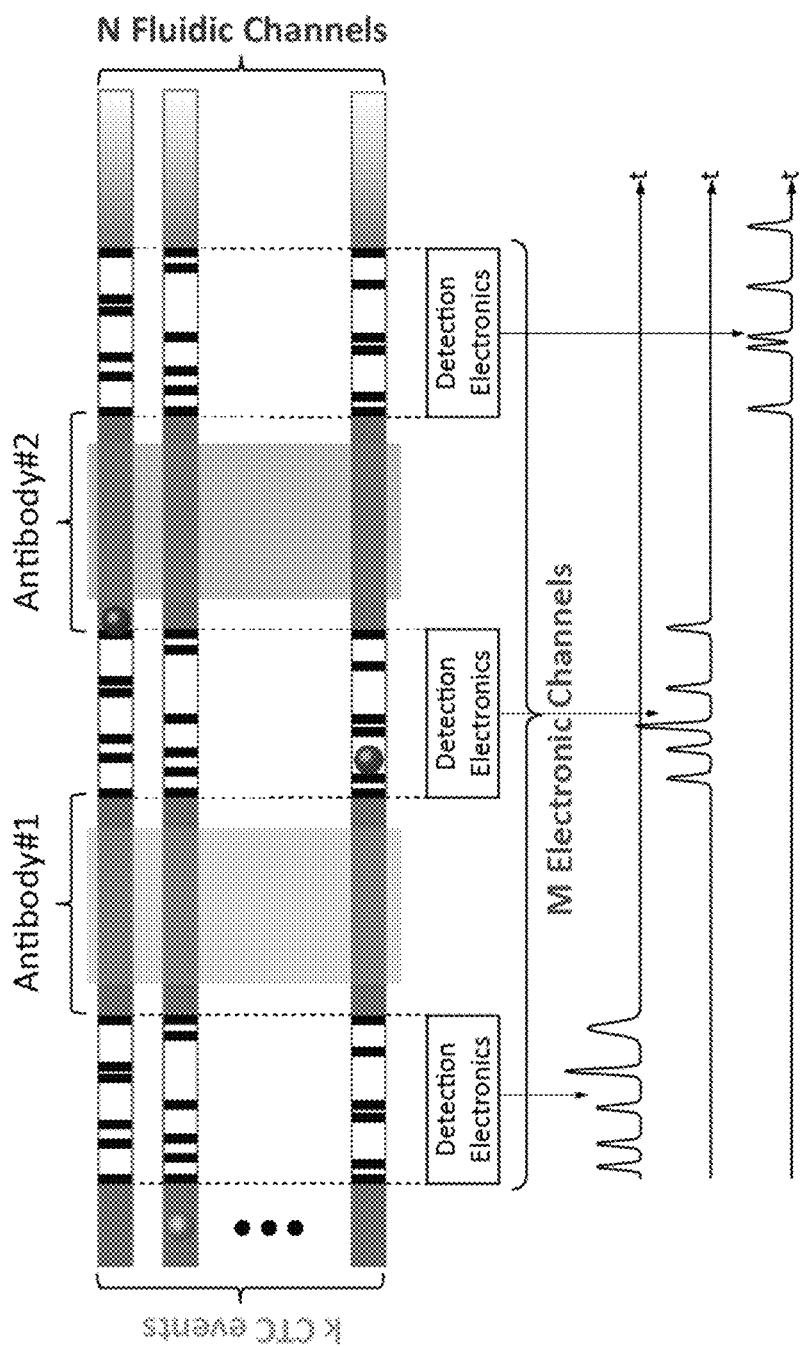
FIG. 6 illustrates parallelized multiple channels with a spatially encoded arrangement of electrodes for transit-time analysis using shared detection electronics.

According to at least some embodiments of the present disclosure, the disclosed system may include a spatially encoded electrode arrangement. FIG. 6 illustrates parallelized multiple channels with a spatially encoded electrode arrangement. In each channel or segment, multiple electrodes are spatially encoded by placing at different location, effectively labeling each microfluidic channel with an identification (ID) number that is unique to the channel. For example, a matched-filtering decoding scheme allows identifying the target cell location. Also, multiple interaction zones are included in each channel, and a spatially encoded arrangement of electrodes may be repeated across the multiple interaction zones, namely the spatially encoded arrangement may be a periodic arrangement.

Thus, FIG. 6 shows an electronic-sharing scheme in massive microfluidics for ultra-high-throughput flow cytometry. Instead of having one detector per fluidic channel, multiple coplanar electrodes are extended across all the microfluidic channels. Impedance measurement is performed on the electrodes, which generates Gaussian-like pulses as cells flow through.

Furthermore, to avoid cell identification ambiguity caused by coupling such an electronic-sharing scheme with multiplexed surface marker detection, the present disclosure describes a coding scheme for designing the electrodes. Prior to the antibody-antigen interaction zone, multiple pairs of electrodes with exact number of electronics are distributed non-uniformly, creating spatially modulated patterns along the fluidic channels. This scheme effectively provides an identification (ID) number to each fluidic channel since the measured pulse train will be position-modulated in time. With the pulse patterns from each fluidic channel, a matched-filter detection scheme is used for mapping groups of electrical pulses with the corresponding cells flowing in the dedicated fluidic channel.

To reduce or mitigate interference, various coding schemes may be used to reduce within-channel autocorrelation and inter-channel cross-correlation. For example, the m-sequence or pseudorandom binary sequence (PRBS) may be used for designing the electrodes. However, m-sequence and PRBS specifies a long code-length, leading to a large number of detection electronics, and may obviate the goal of hardware-efficient design.

According to at least some embodiments of the present disclosure, given the fact that the sequence of the pulses from each fluidic channel is known, a simpler coding scheme such as a three-electrodes configuration can be used. This is due to extra degree of freedom with more than one electronic detector.

Figure 6A:
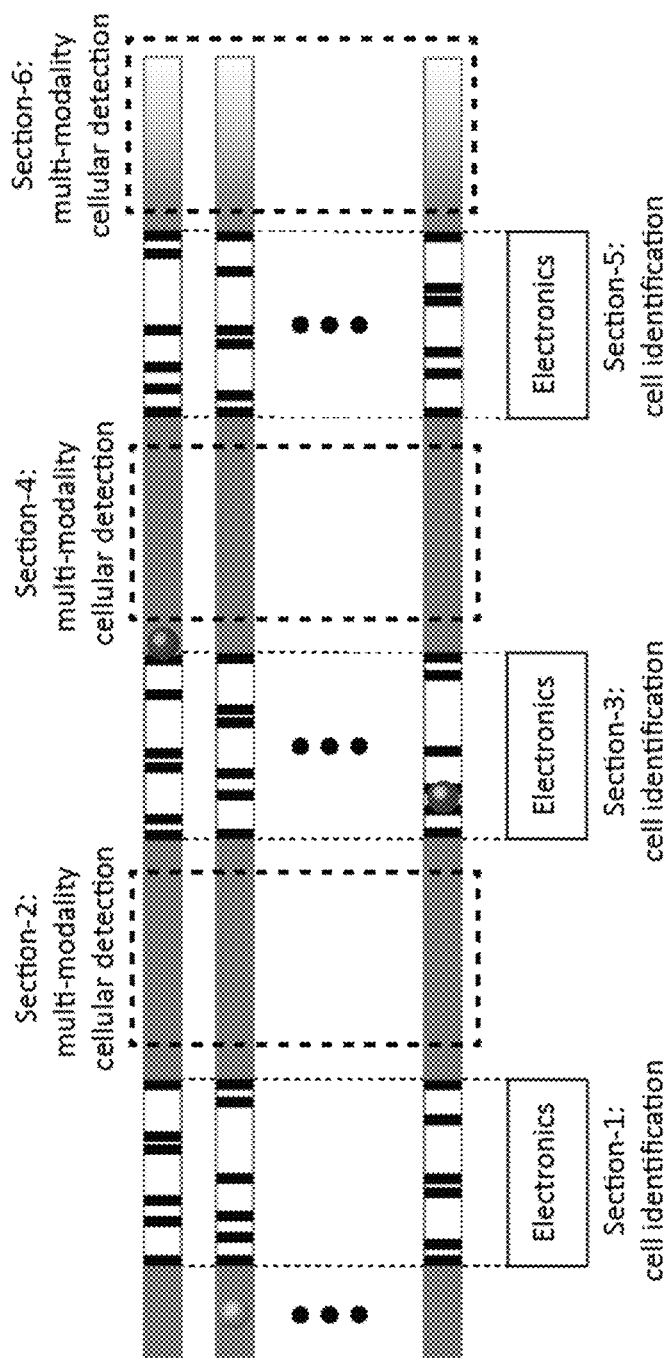
FIG. 6A shows a generalized hardware-efficient electronic-sharing scheme in massive microfluidics for ultra-high-throughput flow cytometry.

In some embodiments, the multiplexed detection technology illustrated in FIG. 6 can be generalized to include identification sections inserted between sections for sample detection section and sample processing. FIG. 6A shows an alternative electronic-sharing scheme in massive microfluidics for ultra-high-throughput flow cytometry. As shown in FIG. 6A, the identification sections (also referred to as interaction zones) are inserted between sections for sample detection section and sample processing (also referred to as detection zones). The identification section provides ID number to each fluidic channel. The sections for sample detection and sample processing are the areas where modulation is introduced to the cells. For example, the modulation can be based on interaction of coated antibodies against the cells, or any suitable detection processes, such as optical sensing, magnetic sensing, acoustic sensing, dielectrophoretic trapping, etc.

Figure 7:
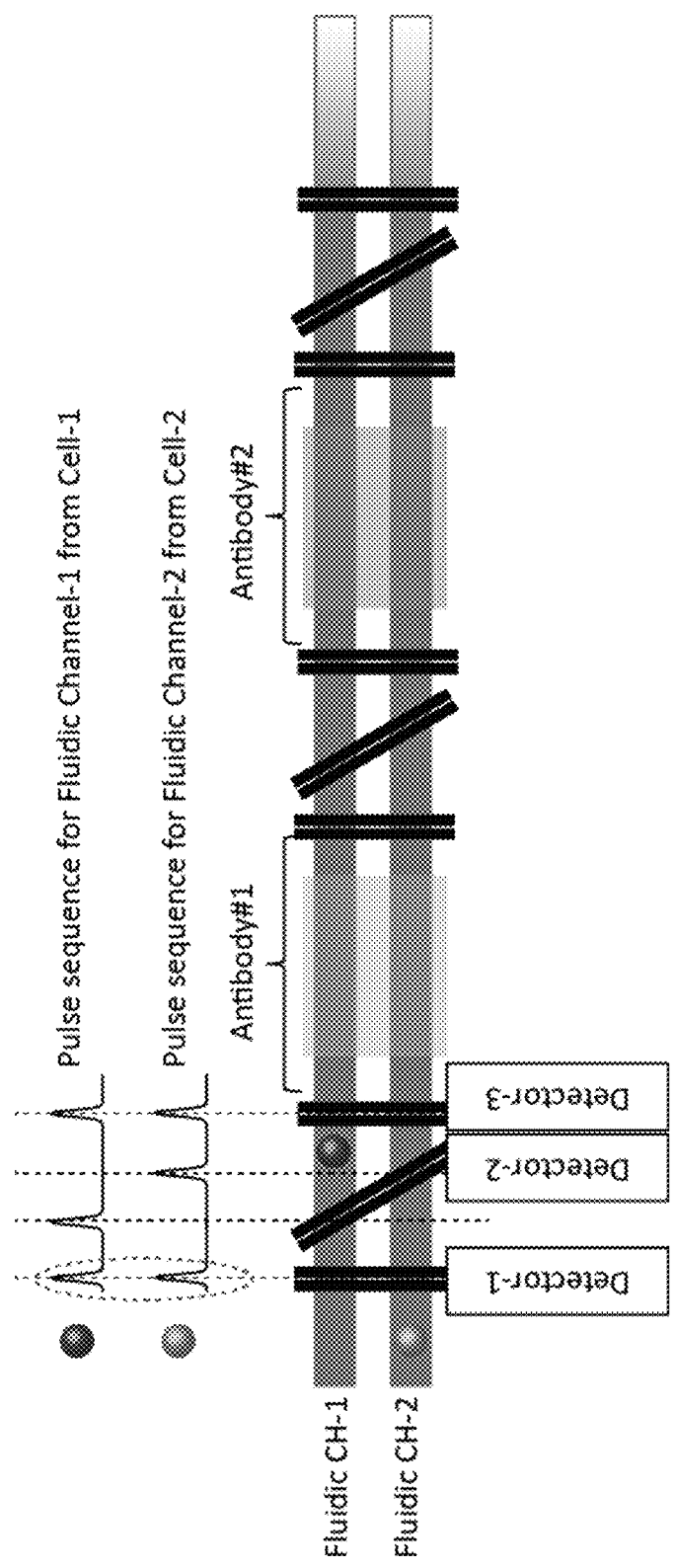
FIG. 7 illustrates an example of multiple sections of three-electrode configuration with spatially encoded arrangement which provides pulse-position-modulated cellular impedance signals.

FIG. 7 illustrates parallelized multiple channels with a cell-specific code library. For example, as shown in the embodiments of FIG. 7, two codes may be different, by offsetting the on-channel location of the center electrode from each other. In some embodiments, the arrangement may create two highly-correlated codes, which may lead to a high interference and a high bit error rate.

In some embodiments, the disclosed system may include mechanisms for reducing or eliminating various sources of errors. The velocity of the cells can exhibit high variation, which can invalidate the library when performing matched-filter decoding. To circumvent this, the templates in the library may be made adaptive by including both the measured pulse height and pulse width.

Figure 8:
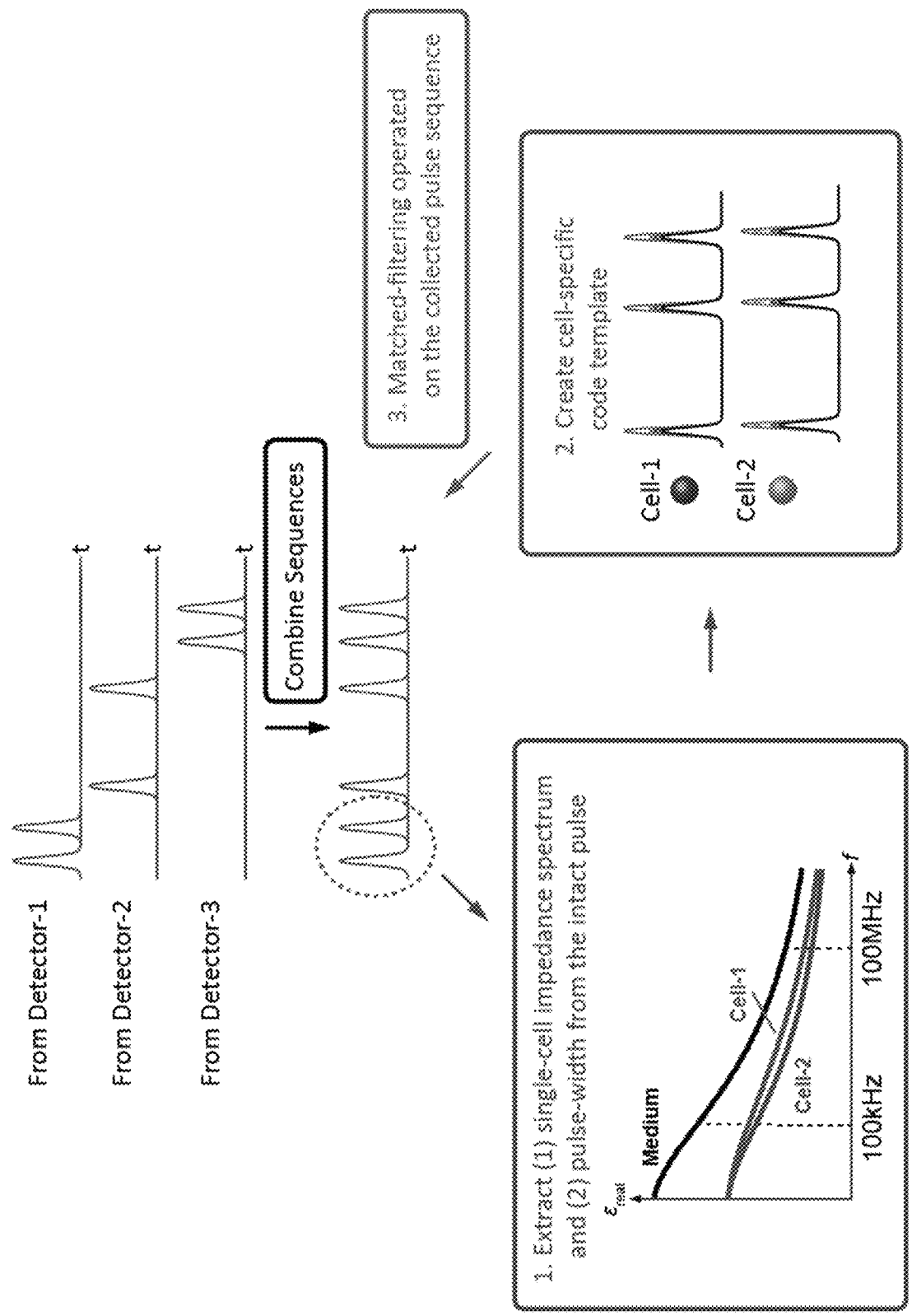
FIG. 8 illustrates a cell-specific library template that increases the signal orthogonality between each cellular signal.

FIG. 8 illustrates a cell-specific library template that increases orthogonality of the codes. As shown in FIG. 8, the process extracts a single-cell impedance spectrum and a pulse width from the intact pulse. The process then creates a cell-specific code template based on the extracted information. A matched-filtering is operated on the collected pulse sequence. Note that, at least in some embodiments, any parameter unique to the cells can be used for creating cell-specific code template. This includes, but not limited to, size and elasticity.

In addition, the frequency dispersion characteristics of each cell can be measured at multiple frequencies. Therefore, a high dimensional code template that is unique to each cell can be formulated in real-time, leading to lower error rate. The same electrode pattern can be replicated in each of the fluidic channel. Alternatively, the codes can be shuffled between different coding zones to further improve the error rate using signal-processing technique such as the majority vote.

In some embodiments, the degree of freedom can be further expanded by introducing deterministic randomness in each of the microfluidic channels. Parameters such as flow rate, and thus cell velocity, can be modulated through the modification of the individual channel geometries (also referred to as "dithering").

Figure 9:
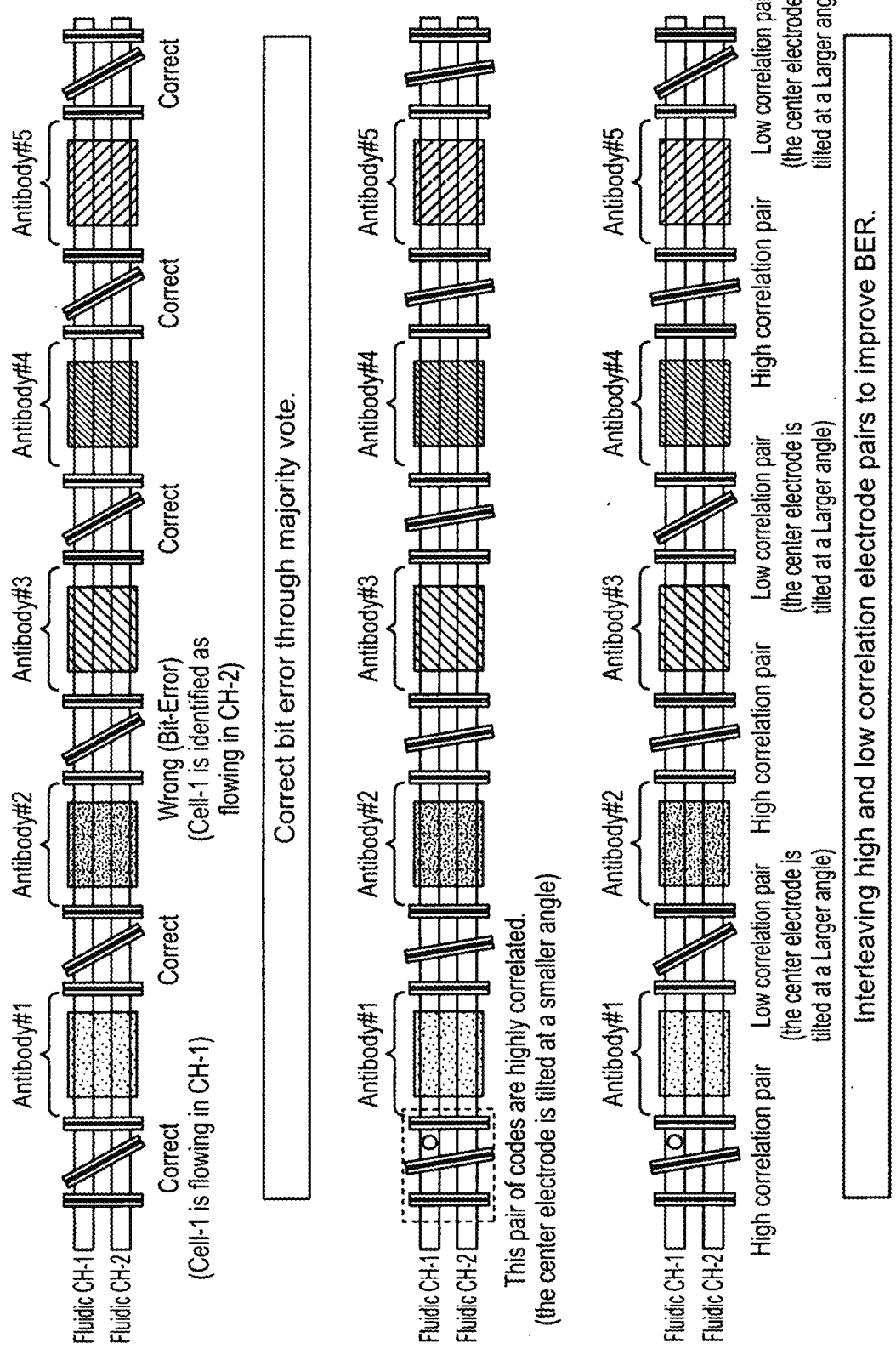
FIG. 9 illustrates a mechanism for improving bit error rate by correcting bit error through majority vote and interleaving high and low correlation electrode pairs.

FIG. 9 illustrates a mechanism for improving bit error rate by correcting bit error through majority vote and interleaving high and low correlation electrode pairs.

Figure 10:
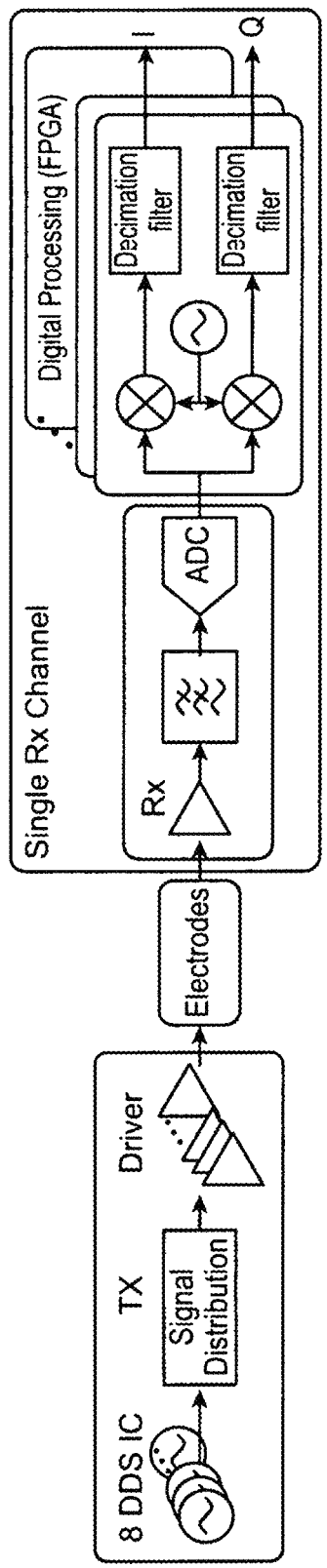
FIG. 10 illustrates an example of electronics for cellular impedance quantification.

FIG. 10 illustrates the electronic components of a microfluidics device for impedance characterization. The microfluidics device may be fabricated using, e.g., polydimethylsiloxane (PDMS) on quartz substrate. Impedance measurements can be implemented using discrete integrated chips (ICs) on a printed circuit board (PCB) or using silicon-based complementary metal-oxide-semiconductor (CMOS) technology. On the transmitting (Tx) side, signal generation may be performed by a direct digital synthesizer (DDS) with a fine frequency resolution or a digital-to-analog converter (DAC) controlled by a field-programmable gated array (FPGA). The excitation signal can either be a single-tone low distortion sinewave, a composition of multi-frequency sinewaves, or a m-sequence pseudo random digital-like broadband signal. On the receiving (Rx) side, a front-end may include a noise-cancelled transimpedance amplifier (TIA). The sampling may be performed at the Nyquist rate or with sub-sampling. Either of, or both, the temperature and flow rates in each individual microfluidic channel can be measured to calibrate the fabrication mismatches and to compensate for the long-term drift.

In some embodiments, a Lab-on-Chip (LOC) system can include multiple building blocks. The blood sample from the patient is diluted with a ratio of, e.g., about 1:2 to about 1:50 without lysing buffers. The diluted samples are injected into the system. The LOC may include multiple sections. The first section is an inertia microfluidic with spiral channels. It performs separation of the smaller red blood cells (RBCs) and platelets from the larger-sized white blood cells (WBCs) and circulating tumor cells (CTCs) at high cellular velocity (e.g., more than about 1 m/sec). Afterward, the flow rate is adjusted through the widening of the fluidic channel. The aim is to lower the flow rate to ensure sufficient interaction time between the cells and the antibodies.

Then, a cascade of multiple 1:2 fluidic splitters separates the single flow into 2N channels. In each fluidic channel, multiple interaction zones can be included for multiplexed surface marker detection. The interaction zones are separated by the ID electrodes. Note that focusing may be used to ensure cells are flowing in close proximity with one of the channel walls. Focusing can be achieved through, but not limited to, dielectrophoresis (DEP). After the detection, targeted cells can be collected for down-stream analysis.

In some embodiments, the disclosed system can perform a high-throughput CTCs sorting with multiplexing capability. The system may process, e.g., about 10 mL of whole blood (may be diluted) in, e.g., about 10 minutes. The system may detect at least 5 different surface markers. The system allows further downstream molecular profiling.

The disclosed system is applicable for liquid biopsy applications, which measures the tumor-related contents in the blood such as circulating tumor cells (CTCs), circulating tumor DNA (ctDNA), and exosomes as indicators for cancer diagnosis. The disclosed system allows higher sampling rate through blood collection, which allows measuring the heterogeneity of the cancer as well as monitoring its dynamics under treatment. At least some of the advantages of the present disclosure include: (1) reduced assay time due to no sample incubation (label-free) and massively parallelized fluidic channels when processing samples with volume on the order of, e.g., tens of mL; (2) multiplexed surface marker detections using simple transit time analysis; (3) reduced number of detection electronics, which can potentially be implemented using, e.g., CMOS (complementary metal-oxide-semiconductor) technology.

Figure 11:
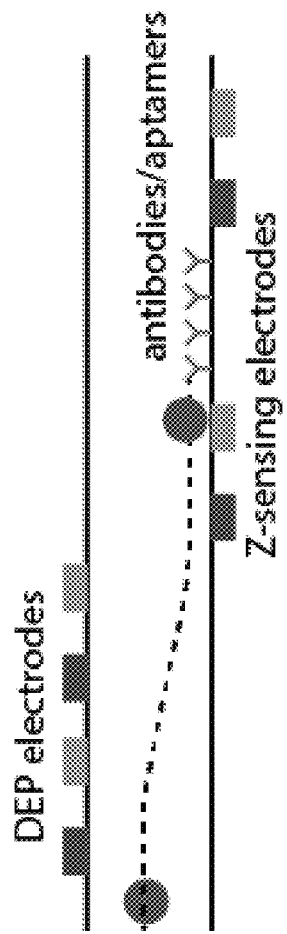
FIG. 11 illustrates the use of dielectrophoresis (DEP) actuation to enhance cellular interaction with surface coated antibodies or other types of molecular recognition molecules.

In some embodiments, positive or negative DEP can be used to ensure sufficient cellular interaction. FIG. 11 illustrates DEP electrodes for cellular interaction. To avoid clogging, fluidic channel may have specified dimensions, e.g., width=about 30 micrometers; height=about 30 micrometers. The channel floor is coated with antibodies and/or aptamers. To ensure sufficient cellular interaction, DEP actuation may be used for attracting or pushing the cells toward the floor. For example, pDEP (positive DEP) may be used to attract the cells; nDEP (negative DEP) may be used to repel the cells. Alternatively, in some embodiments, channel heights may be smaller than the cellular diameters to constrict the cells through hydrodynamic stretching forces, thus promoting maximal cellular interaction.

In some embodiments, inertia sorting may be used for achieving a high throughput for cell sorting. Sorting is based on particle size, and therefore may be suitable for separation of CTC+RBC from RBC. There may be at least three forces in the system of inertia sorting: (1) shear force due to fluidics, (2) lift force from the channel solid sidewall, and (3) centrifugal forces that induces vortices, which push cells laterally along the width of the fluidic channel. Single channel may run at, e.g., about 1.5 mL/min. Parallelization with 16 may run at, e.g., about 24 mL/min. Whole blood has hematocrit around 45%, meaning 45% of blood samples are cells, rest are plasma. The sample may be diluted to reduce the interaction between cells when working with inertia microfluidics. The ratio of dilution ranges may be, e.g., from about 5× to about 100×. For example, assuming 3 mL of whole blood sample from a cancer patient, the whole blood sample can transform into about 15 to about 300 mL of testing samples. In some embodiments, the system can achieve a fast, clean, and automated process without RBC lysing and/or centrifugal filtration.

Figure 12:
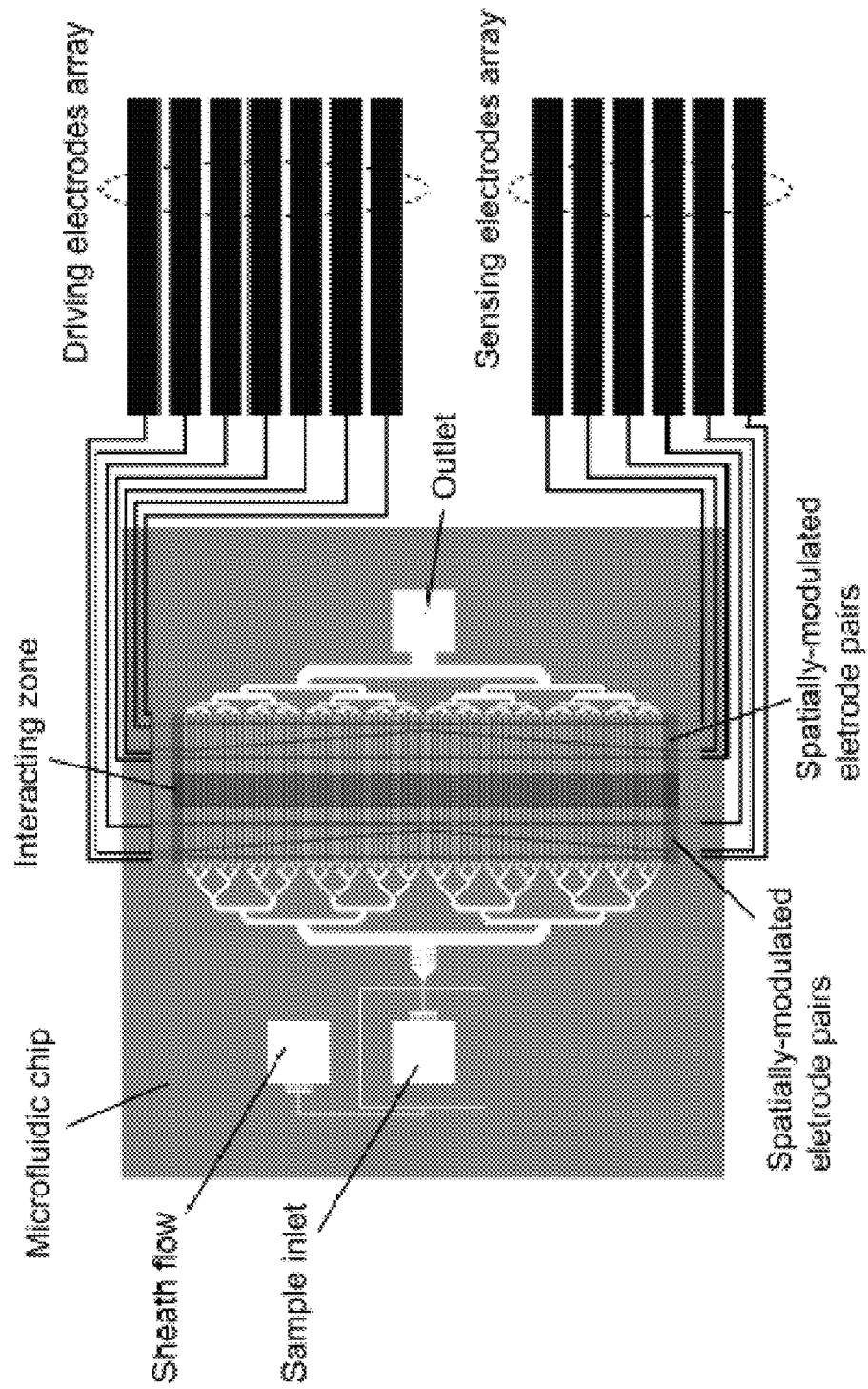
FIG. 12 illustrates a sample microfluidic chip comprising multiplexed microfluidic channels.

FIG. 12 illustrates a sample microfluidic chip comprising multiplexed microfluidic channels. The microfluidic chip comprises 128 multiplexed microfluidic channels with two groups of spatially-modulated electrode pairs and a cellular interaction zone. Arrays of driving electrodes and sensing electrodes are connected to the spatially-modulated electrode pairs.

Figure 13:
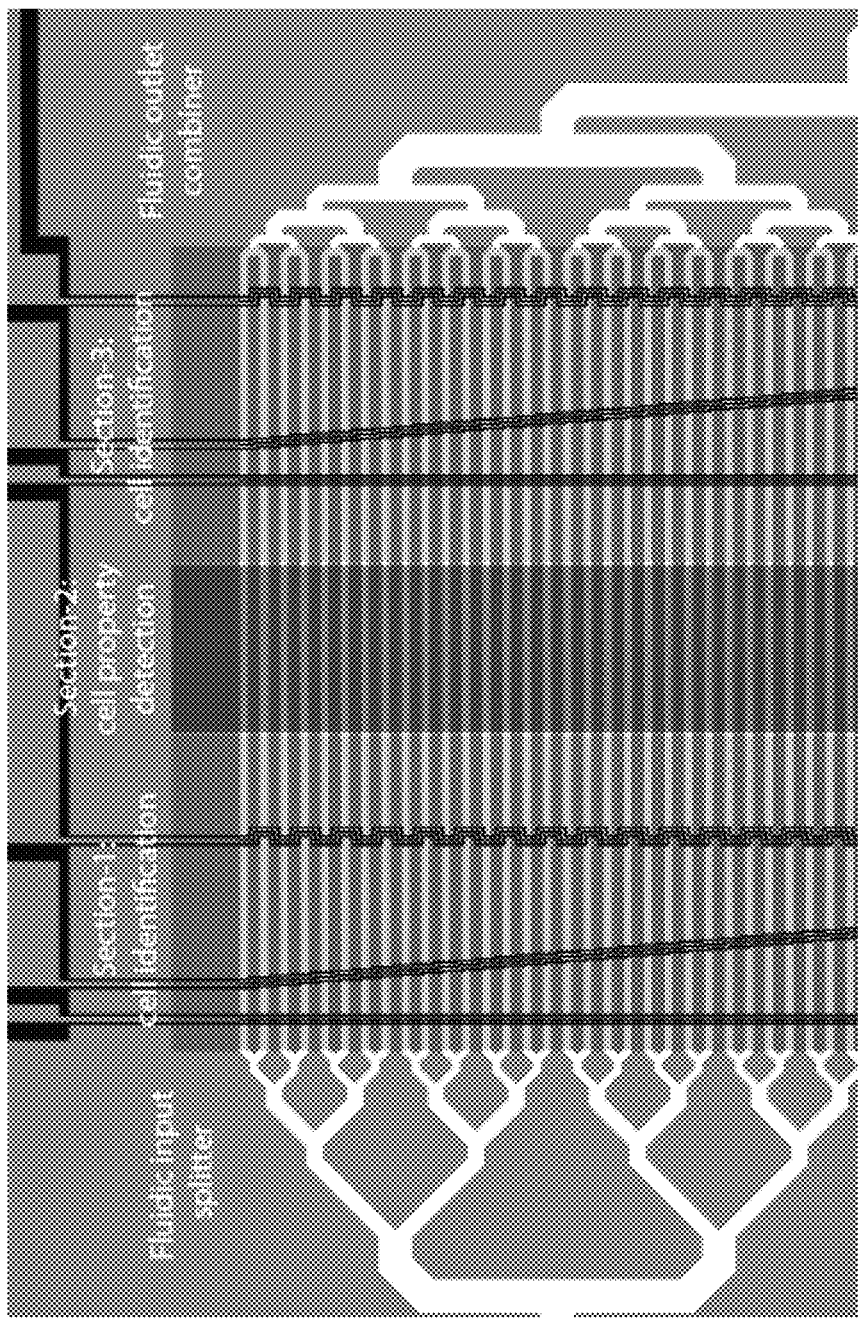
FIG. 13 illustrates a zoom-in view of the microfluidic channels on top of the electrode pairs.

FIG. 13 illustrates a zoom-in view of the microfluidic channels on top of the electrode pairs. In some embodiments, each electrode group includes three (or any other number) pairs of electrodes that are spatially modulated and disposed cross the microfluid channels.

In some embodiments, mechanical property of the cells can be used to create cell-specific template to further enhance the orthogonality. In addition to label-free cytometry, impedance spectroscopy can also be applied for measuring, e.g., the mechanical property of the cells. This can be referred to "deformability cytometry" where shear forces or pressures are applied to the cells and its degree of deformation is quantified.

Figure 14:
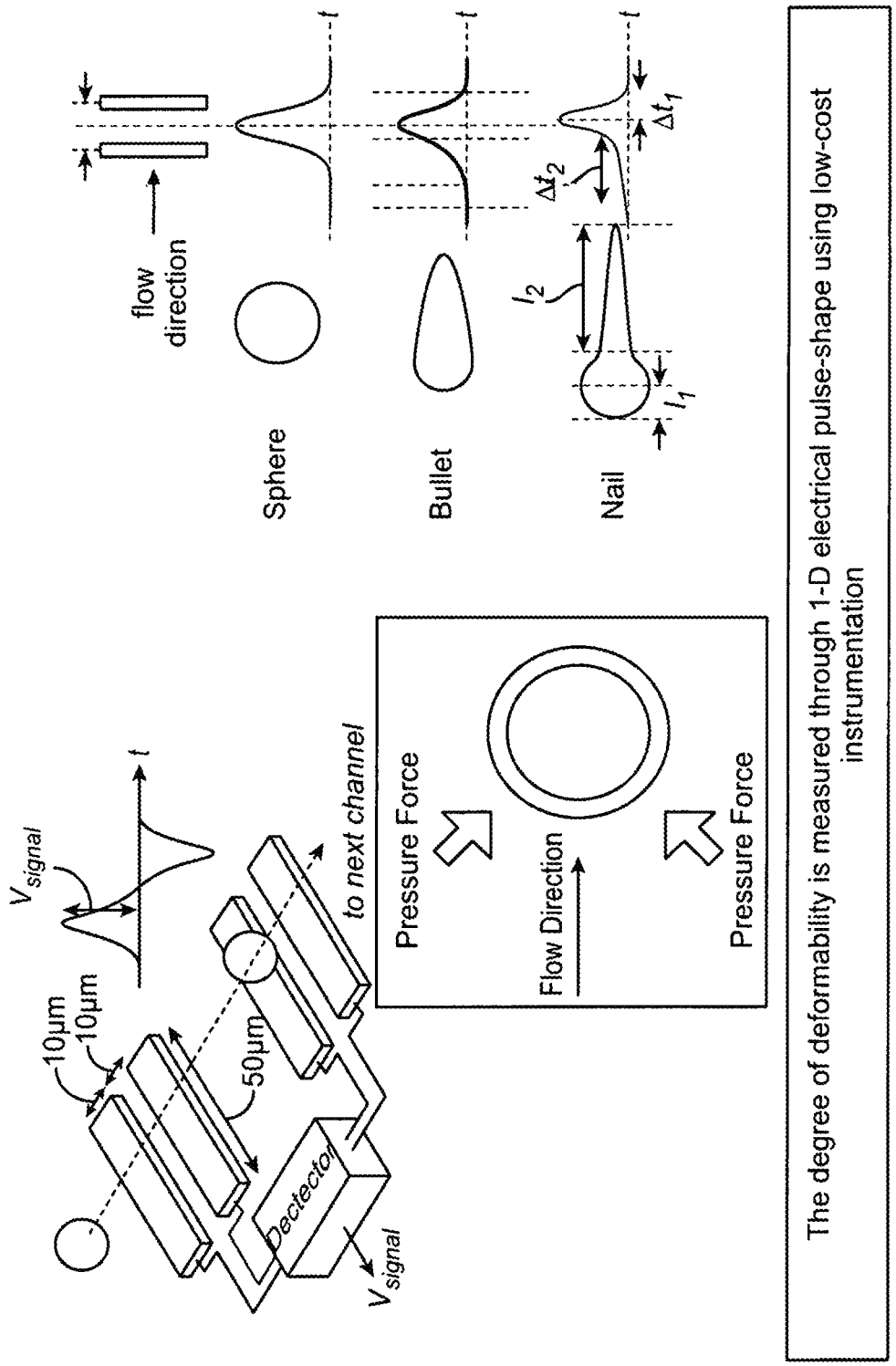
FIG. 14 shows measuring cellular deformability using impedance analysis.

Instead of using high-speed optical camera for this type of measurements, which increases the costs of the system and incurs significant amount of data computation, impedance analysis can quantify the "degree of deformation" by analyzing the changes in the measured electrical pulse shape, which has direct correlation to the changes in the shape of the cells in a flow. FIG. 14 shows measuring cellular deformability using impedance analysis. The degree of deformability can be measured through, e.g., one-dimensional (1-D) electrical pulse using low-cost instrumentation. Thus, instead of using impedance profile to create cell-specific template (e.g., as illustrated in FIG. 7), the pulse shape can be used to create cell-specific template as well.

Figure 15:
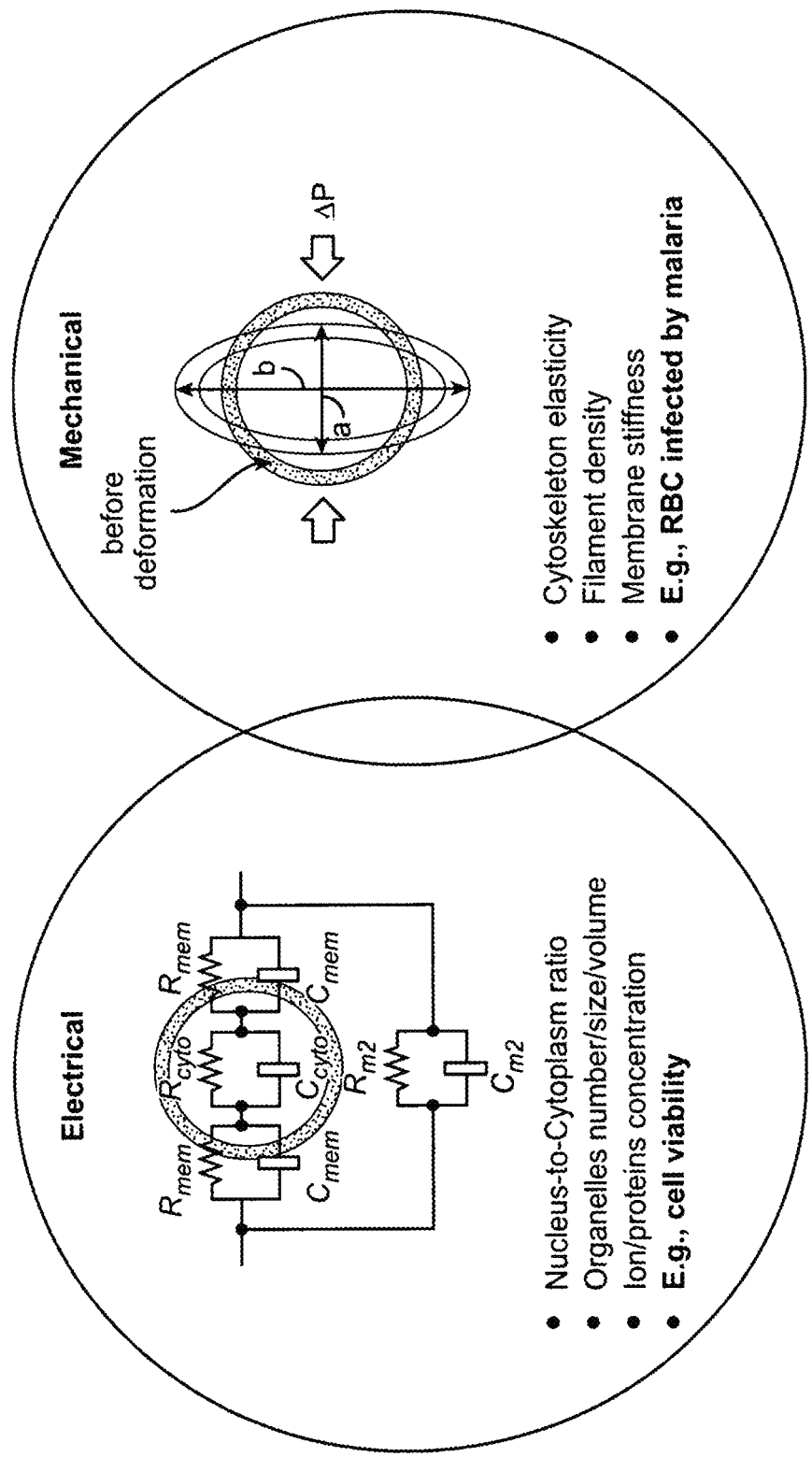
FIG. 15 shows that two physical properties of cells can be used for discrimination.

Thus, the use of cells' impedance spectroscopy to create "cell-specific" template, which, after applying matched filtering, improves the orthogonality between each cell data. The technique can also be applied by using the mechanical properties of the cells. FIG. 15 shows that two physical properties of cells can be used for discrimination.

Figure 16:
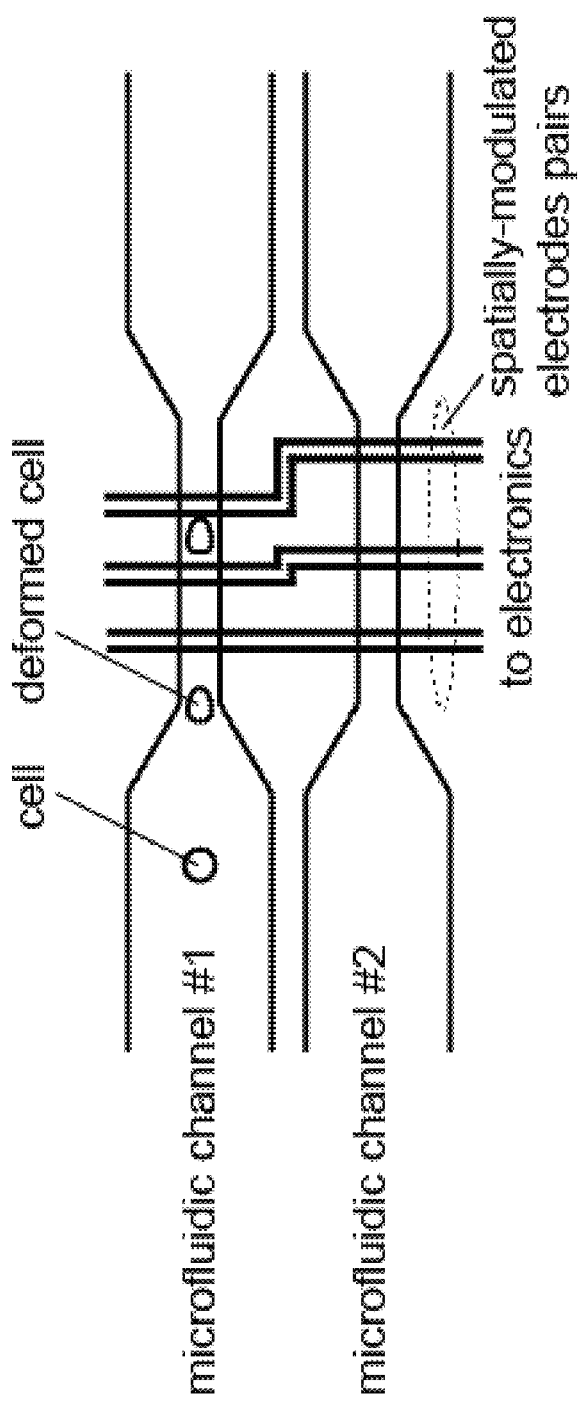
FIG. 16 shows an example of two-channel microfluidic configuration for deformability cytometry.
Figure 17:
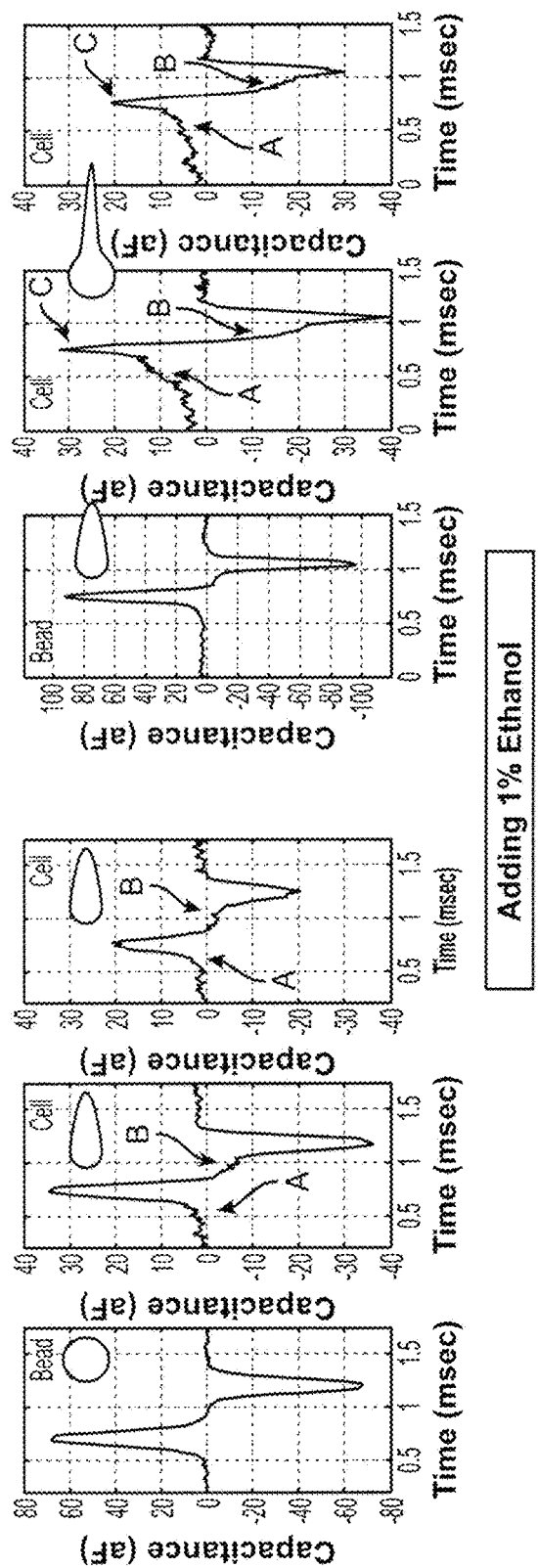
FIG. 17 shows examples of measurement data of deformability cytometry.
Figure 17:
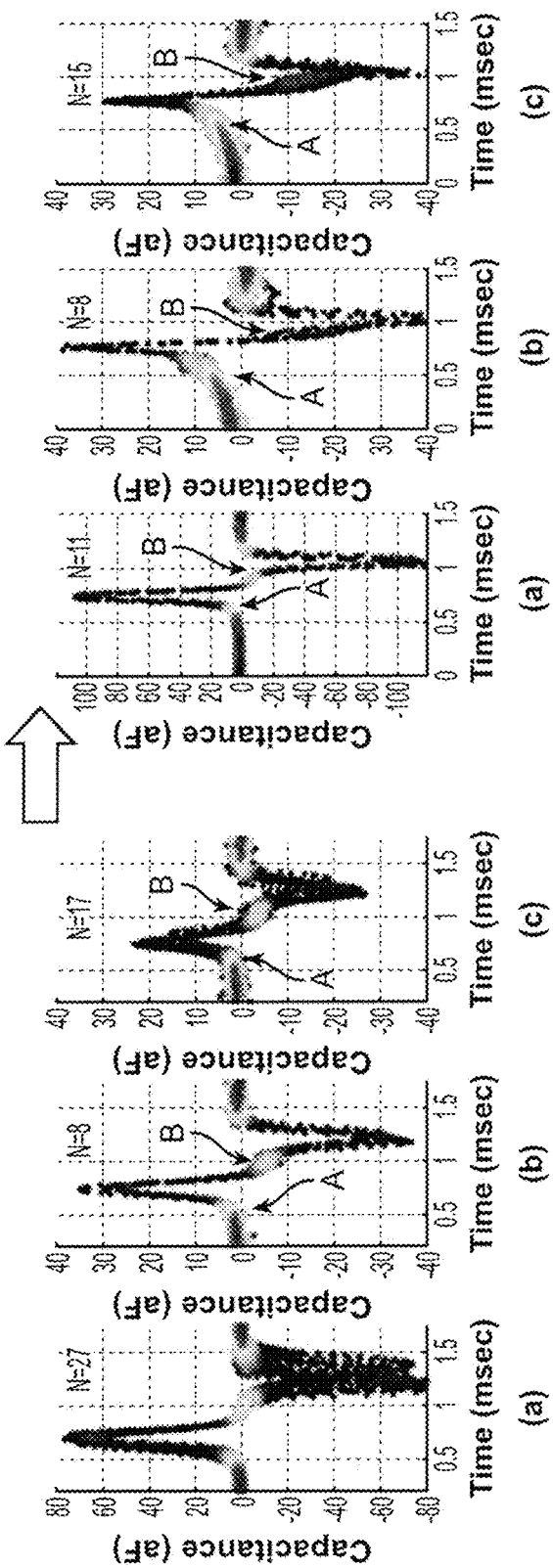

FIG. 16 shows a sample microfluidic configuration for deformability cytometry. As shown in FIG. 16, the cells are deformed in a portion of the microfluidic channels. The shape of the deformed cells cause the sensors of the spatially-modulated electrode pairs to detect different electrical pulse. Thus, the degree of cell deformation can be quantified by the change in the shape of the electrical pulse, and can be used to identify and detect the cell particles. FIG. 17 shows examples of measurement data of deformability cytometry.

Although some embodiments of this disclosure are explained in the context of impedance detection, more generally other modalities can be included. Also, in place of, or in addition to, electrical responses of cells, other cell-specific physical parameters, e.g. elasticity of the cells, can be utilized.

As used herein, the singular terms "a," "an," and "the" may include plural referents unless the context clearly dictates otherwise.

As used herein, the terms "approximately," "substantially" "substantial," and "about" refer to a considerable degree or extent. When used in conjunction with an event or situation, the terms can refer to instances in which the event or situation occurs precisely as well as instances in which the event or situation occurs to a close approximation, such as when accounting for typical tolerance levels of the manufacturing methods described herein. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same or equal if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is understood that such range formats are used for convenience and brevity, and should be interpreted flexibly to include numerical values explicitly specified as limits of a range, as well as all individual numerical values or sub-ranges encompassed within that range, as if each numerical value and sub-range is explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims.

The construction and arrangement of the structures and methods as shown in the various example embodiments are illustrative only. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the example embodiments without departing from the scope of the present disclosure.

What is claimed is:

1. A microfluidics device, comprising:
   an inlet for receiving a fluidic sample including biological particles;
   a plurality of parallelized microfluidic channels disposed across an interaction zone for transit-time analysis of the biological particles;
   a splitter coupled to the inlet and configured for transmitting the fluidic sample into the parallelized microfluidic channels; and
   a plurality of detection electrodes configured to conduct the transit-time analysis, each detection electrode being coupled to all of the parallelized microfluidic channels.

2. The microfluidics device of claim 1, wherein the detection electrodes are spatially encoded electrodes arranged on locations of each of the parallelized microfluidic channels.

3. The microfluidics device of claim 2, wherein the arrangement of locations of the spatially encoded electrodes in each parallelized microfluidic channel represents an identification unique to the parallelized microfluidic channel.

4. The microfluidics device of claim 3, further comprising:
   a decoding component configured to decode the identification of location unique to the parallelized microfluidic channel based on a matched-filtering scheme.

5. The microfluidics device of claim 1, further comprising:
   surface markers targeted to the biological particles disposed on walls of the parallelized microfluidic channels at the interaction zones, the target surface makers reduce flowing velocities of the biological particles.

6. The microfluidics device of claim 1, wherein the interaction zones are between the detection electrodes.

7. The microfluidics device of claim 1, wherein the detection electrodes include at least three electrodes, and on-channel locations of at least one electrode of the detection electrode are offset from each other among the parallelized microfluidic channels.

8. The microfluidics device of claim 1, further comprising:
   dielectrophoresis (DEP) actuation components disposed adjacent to surfaces of the parallelized microfluidic channels, the DEP actuation components attracting the biological particles toward the surfaces or repelling the biological particles away from the surfaces.

9. The microfluidics device of claim 1, further comprising:
   a storage component for storing a cell-specific library including at least a cell-specific library template from based on detected signals of the biological particles, wherein locations of the detection electrodes on the parallelized microfluidic channels depend on the cell-specific library template.

10. The microfluidics device of claim 1, wherein the detection electrodes are configured to perform analysis of biological particles including circulating tumor cells (CTCs), circulating tumor DNA (ctDNA), or exosomes.

* * * * *